United States Patent [19]

Lee et al.

[11] Patent Number: 4,645,494
[45] Date of Patent: Feb. 24, 1987

[54] PERITONEAL DEVICE SYSTEM

[75] Inventors: Jeffrey A. Lee, Maple Grove; Felix J. Martinez, Plymouth, both of Minn.

[73] Assignee: Renal Systems, Inc., Minneapolis, Minn.

[21] Appl. No.: 790,092

[22] Filed: Oct. 22, 1985

[51] Int. Cl.⁴ .............................................. A61M 5/00
[52] U.S. Cl. ..................................... 604/175; 604/29
[58] Field of Search ................ 604/29, 93, 99, 174, 604/175, 249, 256; 128/766

[56] References Cited

U.S. PATENT DOCUMENTS

| 3,469,572 | 9/1969 | Nehring | 128/766 |
|---|---|---|---|
| 3,838,843 | 10/1974 | Bernhard | 128/766 |
| 4,108,174 | 8/1978 | Slivenko | |
| 4,344,435 | 8/1982 | Aubin | 604/175 |
| 4,350,157 | 9/1982 | Hoffa | 604/175 |
| 4,405,320 | 9/1983 | Cracauer et al. | 604/175 |
| 4,417,888 | 11/1983 | Cosentino et al. | |
| 4,425,119 | 1/1984 | Berglund | 604/175 |
| 4,488,877 | 12/1984 | Klein et al. | 604/175 |
| 4,496,349 | 1/1985 | Cosentino | 604/175 |

Primary Examiner—C. Fred Rosenbaum
Assistant Examiner—Michelle N. Lester
Attorney, Agent, or Firm—Vidas & Arrett

[57] ABSTRACT

A system for use in peritoneal dialysis consisting of a rigid tubular implantable device, a stabilizing tool and an access set. The implantable device includes a centrally positioned, outwardly projecting cannula spike whose side openings are normally closed by a resilient sleeve member. A stabilizing tool having a broad load distributing base is locked to an upper flange of the implanted device. An access set connected to a dialysis solution system includes a septum which is penetrable by the cannula spike. Penetration simultaneously depresses the resilient cannula sleeve exposing the side openings which allows fluid flow. The access set, stabilizing tool and implant device are locked together whenever fluid is able to flow between the peritoneal cavity and the dialysis solution system.

6 Claims, 5 Drawing Figures

PERITONEAL DEVICE SYSTEM

DESCRIPTION

1. Field of the Invention

This invention relates to an implantable device for use in peritoneal dialysis. In particular, the invention relates to devices which enables a patient to readily connect and disconnect the dialysis treatment bag and tubing from the implanted device.

2. Background of the Invention

Peritoneal dialysis has been accomplished to date by means of a flexible catheter which has been implanted so as to pass directly through the skin and peritoneal wall and into the peritoneal cavity. A recent detailed review of the devices associated with peritoneal dialysis may be found in Ward et al, "Investigation of the Risks and Hazards With Devices Associated with Peritoneal Dialysis (Including Intermittent Peritoneal Dialysis and Continuous Ambulatory Peritoneal Dialysis) and Sorbent Regenerated Dialysate Delivery Systems". Revised Draft Report for FDA Contract No. 223-81-5001 (June, 1982).

Improvements in peritoneal dialysis implants are described in U.S. Pat. Nos. 4,496,349, 4,488,877 and 4,417,888 all of which have a common assignee with the present application. The improvements of these prior applications comprise rigid, tubular percutaneous devices implanted through the skin to which a catheter member is affixed subcutaneously. Access to the peritoneum in these devices is accomplished through a sterile needle assembly which enters a septum.

In continuous ambulatory peritoneal dialysis, dialysate is kept in the peritoneal cavity continuously. Dialysate is inflowed from a container and allowed to dwell into the peritoneal cavity for five or six hours. The cavity is then drained and fresh bag of dialysate is immediately exchanged. More connect and disconnect procedures are required with continuous ambulatory peritoneal dialysis than with other peritoneal dialysis methods and the risk of infection is commensurately higher. A useful system in continuous ambulatory peritoneal dialysis (hereinafter CAPD) should minimize the effort and time required in connecting and disconnecting the tubing set and bag from the implanted device so as to minimize the risk of infection. Also, the connection and disconnection procedure should minimize any trauma to the tissue immediately surrounding the implanted device since such areas are major infection of routes if damaged.

Continuous cyclic peritoneal dialysis (hereinafter CCPD) resembles CAPD by utilizing continuous peritoneal dialysis. However, a peritoneal dialysis cycling machine is utilized to instill the fluid at night while the patient sleeps. Therefore, the long-dwell cycle occurs during the day time. CCPD involves fewer connect and disconnect procedures than CAPD. However, the benefits to be achieved in CAPD also apply to CCPD.

BRIEF SUMMARY OF THE INVENTION

The present invention consists of an implantable percutaneous device, a stabilizing access tool and an access set which is attachable to standard dialysis tubing. Briefly, the stabilizing access tool is secured about a projecting flange on the external portion of the implant device so as to provide a load distributing base during the connection and disconnection of the access set. The access set is inserted through an opening in the access tool and is locked to the access tool. During insertion, the valve mechanism of the implant device is opened by its contact with the access set to allow flow in or out of the body.

The percutaneous implant device of the invention is especially suitable for all forms of peritoneal dialysis and includes a substantially rigid tubular percutaneous body of biologically compatible material. The distal end of the tubular body extends through the skin when implanted so as to provide a means for accessing the peritoneal cavity through the interior of the device. The proximal end of the tubular body is embedded under the skin line. A catheter extends from the proximal end of the tubular body into the peritoneal cavity. The catheter is preferably held to the tubular body by inserting a wedge-like catheter adapter through the tubular body toward its proximal end such that the flexible catheter tubing is securely held between the tubular body and the catheter adapter. Preferably, the catheter adapter includes an upper flange backed on each side by an O-ring seal.

A cannula spike is positioned within the tubular body above the catheter adapter and seals. The cannula spike comprises a tubular portion having a lower external flange and an upper closed end which may be rounded or pointed. At least one side opening is formed within the tubular portion of the cannula spike below the closed end. The cannula spike is inserted within the tubular body such that the flange rests upon the seal above the catheter adapter and the closed end of the spike projects towards the distal end of the tubular body. The cannula spike is than locked in place by means of a locking ring which fits within a recess formed in the tubular body. The two O-ring seals allow a compression fit of the cannula spike such that a fluid-tight seal is achieved. Fluid passing from the distal portion of the device must pass through the side openings of the cannula spike to enter the lower catheter.

In order to prevent fluid from continuously flowing in or out of the implantable device, a flexible cannula sleeve is positioned over the tubular portion of the cannula spike. One end of the cannula sleeve abuts against the lower flange and the other end extends beyond the side openings in the cannula spike so as to effectively prevent flow therethrough. The cannula sleeve is formed from a flexible material having "memory" such that it will rebound to its original position after deformation. The cannula sleeve fits tightly around the cannula spike preventing fluid flow through the side openings until downward pressure is exerted on top of the cannula sleeve. Downward pressure causes the sleeve to buckle downwardly exposing the side openings. Fluid may then flow through the side openings until pressure is released on the cannula sleeve. The cannula spike and sleeve provides a dependable, normally closed valving mechanism which is very simple and efficient.

In order to provide fluid communication between the dialysate bag and the peritoneal cavity through the implant device, an inventive access set is employed. The access set includes a tubular access cartridge having a distal portion to which the flexible plastic tubing of the dialysis bag connects. The proximal end of the access cartridge is sealed by a septum which may be penetrated by the cannula implant device. The septum is maintained in position by an end cap which is secured to the proximal end of the access cartridge. The end cap provides a guide to align the access cartridge within the interior of the implant device such that it will be centered to pass over the cannula spike. An inner shoulder in the end cap adjacent the septum contacts the end of the cannula sleeve as the access set is inserted into the implant device. The shoulder causes the cannula sleeve to depress downwardly toward the catheter at the same time the cannula spike penetrates the access set membrane. The side openings in the cannula spike are thereby exposed to the fluid within the cavity of the access cartridge to allow fluid flow between the dialysis bag and the peritoneal cavity.

The insertion and removal of the access set from the implant device involves forces which tends to cause the outside of the implant device tubular body to move relative to the epidermis surrounding it. In order to minimize any distruption of the positioning of the implant device within the skin, a stabilizing tool is utilized whenever the access set is used. The stabilizing tool includes a pair of opposing handles held apart by a flexible hinge adjacent its proximal end. Each proximal end of the handle members has opposing semi-circular faces having a central groove therein which may be secured about an upper flange of the implanted device. Each semi-circular face also includes a load distributing platform having a relatively large area which will contact the skin immediately surrounding the implanted device such that pressure from the insertion of the access set into the implant device may be spread over a relatively large skin area to lessen trauma.

Preferably, the stabilizing tool includes an internal retainer lip along the distal edge of the semi-circular faces. This lip may mate with a pair of ears attached to the handle members on the access cartridge. When the access set is inserted through the tool into the implant device, the ears engage the retaining lip thereby locking the access set, tool and implant device together. Release is accomplished by merely squeezing the access handle members together so as to disengage the ears. The stabilizing tool also provides a guide for the access set.

BRIEF DESCRIPTION OF THE DRAWINGS

A detailed description of the invention is hereinafter described with specific reference being made to the drawings in which.

DETAILED DESCRIPTION OF THE INVENTION

Figure 3:
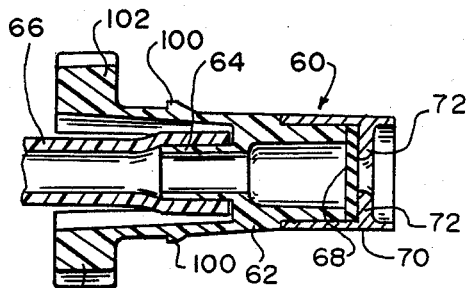
FIG. 3 is a cross-sectional view of the access set of the invention.
Figure 4:
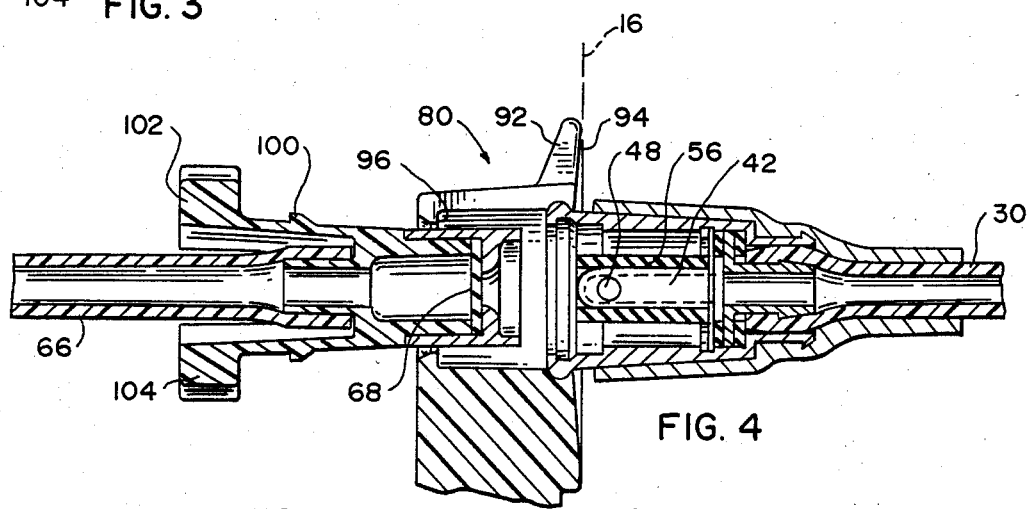
FIG. 4 is a cross-sectional view in which the access set is being inserted through the stabilizing tool into the implant device.
Figure 5:
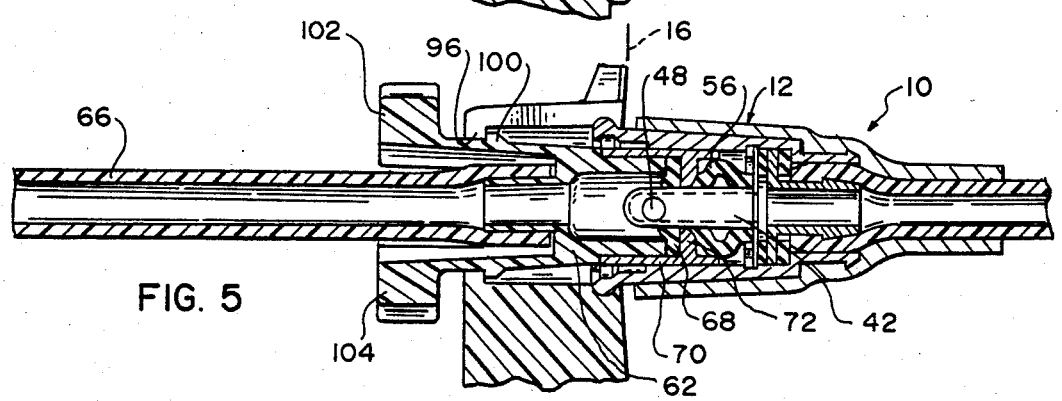
FIG. 5 is a cross-sectional view of the access set, stabilizing tool and implant device locked together so as to allow fluid flow.

The preferred embodiment of the invention is shown in FIGS. 1-5. FIGS. 4-5 in particular shown the invention in use.

A rigid, tubular percutaneous device 10 and attached flexible sleeve member 12 including distal end 14 are implanted between skin layers 16 and the peritoneal wall 18. Rigid, tubular body 10 is preferably made of titanium which may be coated with vapor-deposited carbon or other biocompatible coatings. Alternatively, body 10 may remain uncoated.

Tissue ingrowth media is affixed to the exterior of body 10 as a porous flexible sleeve member or cuff 12. Flexible sleeve member 12 serves as a tissue ingrowth media which stabilizes the implant and prevents its extrusion. Flexible sleeve 12 is preferably made of a material such as the expanded polyethylene terephthalate sold under the trademark Dacron ® by E. I. DuPont deNemours of Wilmington, Del. and high porosity polytetrafluoroethylene.

Better ingrowth is found when flexible sleeve member 12 which contacts the epidermis 23 is formed of an expanded, 90 to 120 pore polytetrafluoroethylene material such as material sold under the trademarks Goretex ® by W. L. Gore Company of Newark, Del. or Impragraph ® by Impra, Inc. of Tempe, Ariz. The polytetrafluoroethylene portion 20 of flexible sleeve member 12 preferably extends from slightly below skin line 16 and extends just inside the dermis shown at 22. The polytetrafluoroethylene (hereinafter referred to as "PTFE") portion 20 of flexible sleeve member 12 is preferably about 1-8 millimeters in width. This compares to a typical epidermis depth of about 0.05 inches (13 mm). The PTFE portion 20 extends to where the polyethylene terephthalate portion 24 begins.

Catheter guide or conduit 26 extends proximally from the proximal end of tubular body 10. Catheter conduit 26 is preferably formed of a low porosity PTFE as described above such as has been commonly used in prior art for indwelling blood access prosthesis used in hemodialysis. Preferably, catheter conduit 26 is about a five inch long (12.7 mm) tube which is slipped over the proximal end of tubular body 10 where it is held in place by mechanical means in addition to a friction fit on ridge 28.

Catheter conduit 26 provides an open passageway through which catheter 30 is inserted. Catheter conduit 26 povides a guide for catheter 30 and facilitates removal of catheter 30 from the implant by preventing internal tissue ingrowth to the catheter 30. Conduit 26 is normally trimmed to end at the peritoneal wall 18, to which it is preferably sewn thereto.

Figure 1:
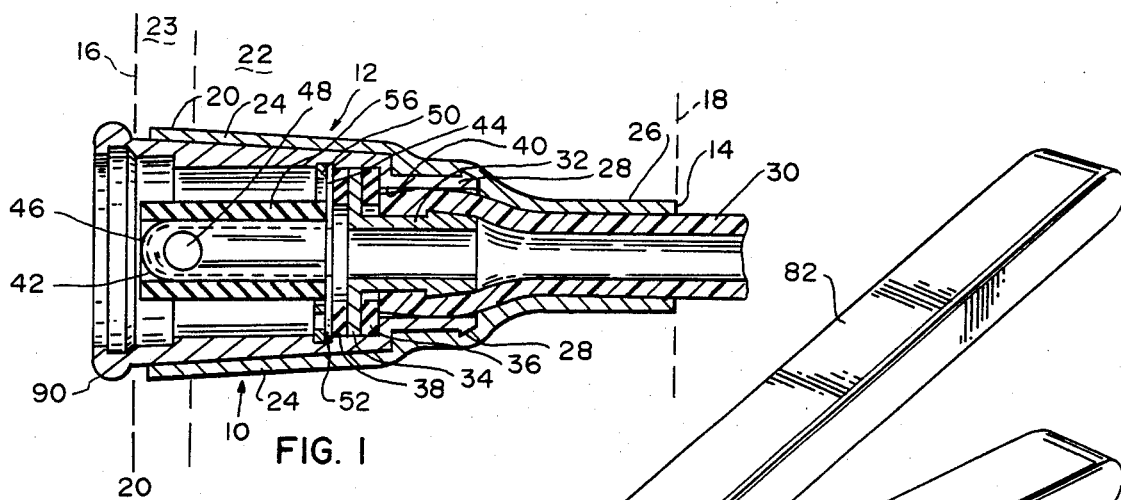
FIG. 1 is a cross-sectional view of an implanted percutaneous device of the invention.

Catheter 30 extends from the proximal end of device 10 and is perfectly formed of a medical grade silicone elastomer. A distal end portion of catheter 30 is preferably held to device 10 by a wedge-like catheter adapter as shown in FIG. 1. Catheter adapter 32 is preferably formed from a titanium based alloy such as the alloy sold under the trademark Renaloy ® by Renal Systems, Inc. of Minneapolis, Minn. Catheter adapter 32 includes an upper flange 34. A fluid-tight seal is formed by placing O-ring seals 36 and 38 as shown in FIG. 1 such that O-ring seal 36 contacts a shoulder 40 within device 10 and upper flange 34. Downward compression applied to O-ring seals 36 and 38 prevents fluid from flowing to the outer surface of catheter adapter 32. O-ring seals 36 and 38 are preferably formed of the 50±5 durometer C-FLEX ® brand polymer of Concept, Inc.

The cannula spike 42 is positioned within the tubular body 10 above catheter adapter 32 and seals 36 and 38. Cannula spike 42 comprises a tubular portion having a lower external flange 44 and an upper closed end 46 which may be rounded or pointed. At least one side opening 48 is formed through the tubular portion of the cannula spike below the closed end as shown in FIGS. 1, 4 and 5. The cannula spike is locked into place by means of a locking ring 50 which fits within a recess 52 formed in tubular body 10. O-ring seals 36 and 38 allow a compression fit of the cannula spike such that a fluid-tight seal is achieved. Fluid passing from the distal portion of device 10 must pass through side openings 48 of the cannula spike to enter catheter 30.

Preferably, cannula spike 42 is formed from a titanium alloy and may be of the same material which forms device 10 and catheter adapter 32.

A flexible cannula sleeve 56 is positioned over the tubular portion of the cannula spike 42. Cannula sleeve 56 is preferably formed of a medical grade silicone of approximately 50 durometers in hardness. The proximal end of cannula sleeve 56 abuts against the lower flange 44 of cannula spike 42. The distal end of cannula sleeve 56 extends beyond side openings 48 of the cannula spike so as to effectively prevent flow therethrough. The cannula sleeve fits tightly around the cannula spike which prevents fluid flow through the side openings 48 in the normal position of the sleeve. The cannula sleeve material is flexible and has a "memory" such that it will rebound to its original position after deformation. Downward pressure applied to the distal end of sleeve 56 causes the sleeve to buckle downwardly exposing side openings 48. Fluid is then able to pass through side openings 48 until pressure is released on the cannula sleeve. The cannula spike and sleeve thereby provides a dependable, normally closed valving mechanism which is very simple and efficient.

An access set 60 is employed to provide fluid communication between a dialysis bag and the peritoneal cavity through the implant device 10. The access set as shown in FIGS. 3-5 includes a tubular access cartridge 62 having a distal portion 64 to which the flexible plastic tubing 66 of a dialysis bag (not shown) connects.

The proximal end of the access cartridge 62 is sealed by a septum 68 formed of silicone rubber or latex. Septum 68 is penetrated by closed end 46 of cannula spike 42. Septum 68 may include a slit therethrough to facilitate insertion of cannula spike 42 through the septum. The septum is maintained in position by a end cap 70 secured to the proximal end of access cartridge 62 by friction or adhesive. End cap 70 includes an inner shoulder 72 as shown in FIGS. 3, 4 and 5 which contacts the distal end of cannula sleeve 56 when access set 60 is inserted into the implant device. The end cap 70 also functions as a guide to align the access cartridge within the interior of the implant device. When access set 60 is inserted into implant device 10, inner shoulder 72 abuts against the cannula sleeve depressing same downwardly toward the catheter at the same time the cannula spike penetrates the access set septum 68. Side openings 48 in the cannula spike 42 are thereby exposed to fluid within the cavity of the access cartridge 62 to allow fluid to flow between the dialysis bag and the peritoneal cavity.

Implant devices are held in place to the human body by tissue ingrowth media encircling the implant device 10. Insertion and removal of access set 60 from the implant device involves forces which tend to cause the outside of the implant device to move relative to the epidermis surrounding it. Any disruption of the tissue ingrowth is highly undesirable since it may allow extrusion of the device or infection to develop about the implant.

Figure 2:
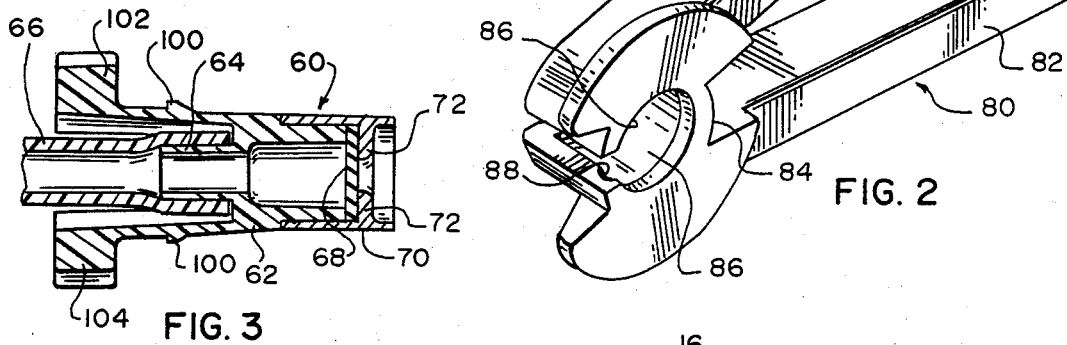
FIG. 2 is a perspective view of the stabilizing tool of the invention.

A stabilizing tool 80 is utilized in conjunction with the implant device 10 and access set 60. The stabilizing tool 80 includes a pair of opposing handles 82 held apart by flexible hinge 84 as shown in FIG. 2. Preferably, stabilizing tool 80 is formed of an acetal resin based copolymer such as the polymers sold under the mark Celcon ® sold by Celanese Chemical Company of New York, N.Y. Each proximal end of handles 82 includes an opposing semi-circular face 86 having a central groove therein which may be secured about an upper flange 90 of implant device 10.

As shown in FIGS. 3-5, each semi-circular face 86 includes a load distributing platform 92 having a relatively large lower planar surface 94. In use, an operator pushes opposing handles 82 together which increases the distance between semi-circular faces 86 of stabilizing tool 80. The tool may then be positioned over upper flange 90 of the implant device 10. Release of the handles causes the flexible hinge 84 to return to its original position which locks upper flange 90 into central groove 88 between semi-circular faces 86. Lower planar surface 94 rests on top of the skin surrounding the implant device. Insertion and removal forces created by the use of the access set are thereby distributed across the contact point of skin to the load distributing platform 92. This greatly lessens any possibility of disrupting the embedment of device 10.

Preferably, stabilizing tool 80 includes an internal retainer lip 96 along the distal edge of the semi-circular faces 86. Retainer lip 96 is configured such that it may mate with a pair of ears 100 attached to handle members 102 and 104 which are secured to the access cartridge 62 as shown in FIGS. 3-5. Preferably, access cartridge 62 includes handle members 102 and 104 is formed from a relatively rigid plastic such as polyvinylchloride. This construction enables an operator to squeeze handle members 102 and 104 toward each other such that ears 100 are able to pass into stabilizing tool 80. Release of the handle members causes them to rebound outwardly such that ears 100 will be in locking engagement with retainer lip 96 of stabilizing tool 80. In this manner, the access set 60 is locked to the stabilizing tool 80 which is in turn locked to the implanted tubular percutaneous device 10.

In operation, stabilizing tool 80 is locked to upper flange 90 of the implant device as shown in FIGS. 4 and 5. Preferably, an operator continues to hold opposing handles 82 of the stabilizing tool while the access set is inserted therethrough. The distal ends of the semi-circular faces 86 tends to act as guide for the access set which is inserted through the stabilizing tool into the implant device 10. As inner shoulder 72 contacts the distal end of cannula sleeve 56, closed end 46 of cannula spike 42 begins to penetrate septum 68. Continued insertion of the access set cause flexible cannula sleeve 56 to deform and collapse proximally as shown in FIG. 5 which exposes side opening 48. This allows fluid to pass from the access set to the catheter and vice versa. Access set 60 is inserted until ears 100 pass retainer lip 96. Access set 60 has a compression fit due to the resiliency of cannula sleeve 56 and O-rings 38 and 36. This combined resilience tends to expel access set 60 which causes ears 100 to be firmly secured against retainer lip 96.

As long as the access set is locked to the stabilizing tool 80 and tubular percutaneous device 10, fluid may pass freely between the dialysis solution bag and the peritoneal cavity. Normal movement of the patient or the dialysis bag set causes forces to be exerted against the implanted access device 10. The stabilizing tool tends to limit the detrimental effects of such forces by distributing the forces across the large surface area of the load distributing platform 92. Also, if an operator holds onto opposing handles 82 of stabilizing tool 80 during insertion or removal of the access set, the operator may counter balance the insertion or removal forces which would otherwise be transmitted to the inner face between the epidermis, dermis and the implant device 10.

The unique combination of the implant device with the stabilizing tool and access set provides a system which greatly lessens damage and possible infection around the embedment of the device. The novel normally closed valving mechanism created by the cannula and cannula sleeve cooperate with the access set to create a simple, reliable means for controlling the flow of fluid to and from the peritoneal cavity.

In considering this invention, it must be remembered that the disclosure is illustrative only and that the scope of the invention is to be determined by the appended claims.

What is claimed is:

1. A percutaneous implant device especially suitable for peritoneal dialysis applications, the device comprising:
    (a) a substantially rigid tubular percutaneous body of biologically compatible material which extends through the skin when implanted so as to provide means for accessing the peritoneal cavity through the interior of said device, said body having a distal end and proximal end, the proximal end being nearest the peritoneal cavity when implanted, said distal end including an outer flange about its circumference;
    (b) flexible subcutaneous catheter means in fluid-tight communication with the interior of said tubular body for providing fluid communication between an animal body exterior and said animal's peritoneal cavity;
    (c) cannula means for controlling flow through said tubular body, said cannula means including a rigid tubular member having a closed end and at least one opening in the side wall of said tubular member adjacent said closed end, said tubular member being positioned within said tubular body such that said closed end faces the distal end of said tubular body, the open end of said tubular member being in fluid-tight communication with said tubular body such that all fluid passing from the distal end to the proximal end of said tubular body must pass through said openings in said cannula means; and
    (d) flexible cannula sleeve means providing a normally closed seal over said cannula means side openings, said sleeve means including a tubular, flexible sleeve member having a smaller inside diameter than the outside diameter of said cannula tubular member, said sleeve member being positioned over and around said tubular member from the proximal end of said tubular member and distally so as to normally completely cover and seal said tubular member side wall openings; said cannula means, rigid tubular percutaneous body and flexible sleeve member being constructed and arranged such that pressure exerted on the distal end of said sleeve member will cause same to collapse downwardly and outwardly such that said sleeve member no longer provides a seal over said tubular member side wall openings, said flexible sleeve member being highly resilient so as to return to its original sealing postion when such pressure is released.

2. The device of claim 1 in combination with percutaneous implant device access means for providing fluid communication between said percutaneous implant device and an external peritoneal dialysis bag, said access means comprising:
    (a) an access cartridge defining an internal passageway for fluid between its distal and proximal ends, said distal end including means for connecting to tubing so as to provide fluid communication between said tubing and said access cartridge;
    (b) end cap means for insertion into said percutaneous implant device so as to depress said sleeve member to provide fluid communication through said percutaneous implant device, said end cap means including a rigid tubular portion having inner and outer diameters sized so as to allow said end cap to freely pass over said cannula means and sleeve member and pass into said tubular percutaneous body, said end cap further including means within the tubular portion projecting inwardly which will abut with the distal end of said sleeve member but not said cannula means when said end cap is inserted into the tubular percutaneous body; and
    (c) septum means for sealing the passageway of said access cartridge, said setpum means including an elastomeric septum member and means for holding said septum member in a sealing relationship adjacent said tubular portion projection means such that upon insertion of said end cap with in said rigid tubular percutaneous body, said closed end of said cannular tubular member may pass through said setpum member such that the openings in said tubular member side walls are within the passageway of said access cartridge distally of said septum member which thereby allows fluid flow between said access means and percutaneous implant device.

3. The device of claim 1 in combination with tool means for stabilizing said percutaneous implant device during access with said access means, said tool means comprising:
    (a) a pair of opposing handle members having proximal and distal ends, said handle members being joined adjacent their proximal ends with a hinge means for allowing the separation between the handle ends to be varied;
    (b) the proximal ends of said handle members having opposing semi-circular faces, each said face having a central groove therein the radius and width of which are substantially equal to the radius and width of said implant device distal end flange; and
    (c) the proximal ends of said handle members further including stabilizing platform means for providing a load distributing platform on the skin surrounding the implanted percutaneous device of claim 1, said platform means including an enlarged flange member having a proximal planar, skin contacting surface to distribute pressure from the insertion of an access means into a percutaneous implant device over a relatively large skin area surrounding the implanted device.

4. The combination of claim 3 wherein said hinge means is a flexible connection between said handle members which normally retains said opposing semi-circular faces in a position such that the distance between said faces is less than the external diameter of said implant device, and the flexible connection is constructed and arranged such that pressing said distal ends of said handle members toward each other increases the distance between said faces such that said faces may be positioned over said implant device and release of said pressure causes said semi-circular faces to return to their normal spaced position.

5. The combination of claim 3 in cooperating combination with opercutaneous implant device access means, said access means comprising:
   (a) accesses cartridge defining an internal passageway for fluid between its distal and proximal ends, said distal end including means for connecting to tubing so as to provide fluid communication between said tubing and said access cartridge;
   (b) end cap means for insertion into said percutaneous implant device so as to depress said sleeve member to provide fluid communication through said percutaneous implant device, said end cap means including a rigid tubular portion having inner and outer diameters sized so as to allow said end cap to freely pass over said cannula means and sleeve member and pass into said tubular percutaneous body, said end cap further including means within the tubular portion porjecting inwardly which will abut with the distal end of said sleeve member but not said cannula means when said end cap is inserted into the tubular percutaneous body; and
   (c) septum means for sealing the passageway of said access cartridge, said septum means including an elastomeric septum member and means for holding said septum member in a sealing relationship adjacent said tubular member side walls are within the passageway of said access cartridge distally of said septum member which thereby allows fluid flow between said access means and percutaneous implant device;

the cooperating combination including means for locking said access means to said tool means, said locking means comprising:
   (a) a retainer lip member projecting inwardly of each of said semi-circular faces along the upper circumference of said semi-circular faces; and
   (b) said access cartridge including a pair of opposing handle members connected to the distal end of said access cartridge, said handle members extending parallel to the longitudinal axis of said access cartridge, said handle members each further including ear members projecting outwardly from the longitudinal axis of said access cartridge and being constructed and arranged such that insertion of said access cartridge into said tool means is accomplished by squeezing said access cartridge handle members together until said ears may pass said retainer lip members, release of said squeezing pressure causing said access cartridge handle members to spring outwardly from the access cartridge longitudinal axis, thereby locking said ears against said semi-circular faces adjacent said retainer lip members so as to prevent disengagement of said access means and tool means until said access cartridge handle member are squeezed together to release the locking relationship.

6. The cooperating combination of claim 5 wherein said retainer lip member of said semi-circular faces is bevelled inwardly from the distal end so as to define a guide for said access means.

* * * * *